(12) United States Patent
Liu et al.

(10) Patent No.: US 9,044,010 B2
(45) Date of Patent: Jun. 2, 2015

(54) STABLE AQUEOUS SUSPENSION CONCENTRATE FOR DELIVERY OF UV-LABILE WATER-INSOLUBLE BIOCIDES

(75) Inventors: Xianbin Liu, Dublin, CA (US); Karen Winkowski, Springfield, NJ (US); Kolazi S. Narayanan, Wayne, NJ (US); Jean-Jacques Gulka, Pine Brook, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 12/966,623

(22) Filed: Dec. 13, 2010

(65) Prior Publication Data

US 2011/0081555 A1 Apr. 7, 2011

Related U.S. Application Data

(63) Continuation of application No. 11/388,553, filed on Mar. 24, 2006, now abandoned.

(51) Int. Cl.
| | | |
|---|---|---|
| *A01N 25/04* | (2006.01) |
| *A01N 25/22* | (2006.01) |
| *A01N 25/30* | (2006.01) |
| *A01N 47/12* | (2006.01) |
| *A01N 59/16* | (2006.01) |
| *A01N 47/04* | (2006.01) |
| *A01N 37/34* | (2006.01) |
| *A01N 43/653* | (2006.01) |
| *A01N 43/80* | (2006.01) |
| *A61K 31/325* | (2006.01) |
| *A61K 31/425* | (2006.01) |
| *C09D 5/14* | (2006.01) |

(52) U.S. Cl.
CPC .............. *A01N 25/04* (2013.01); *A01N 25/22* (2013.01); *A01N 59/16* (2013.01); *A01N 25/30* (2013.01); *A01N 47/12* (2013.01); *A61K 31/325* (2013.01); *A61K 31/425* (2013.01); *C09D 5/14* (2013.01)

(58) Field of Classification Search
CPC ....... A01N 25/04; A01N 25/30; A01N 47/12; A01N 47/04; A01N 43/80; A01N 43/653; A01N 37/34; A01N 2300/00; A01N 25/22; A01N 59/16; A61K 31/325; A61K 31/425; C09D 5/14
See application file for complete search history.

(56) References Cited

U.S. PATENT DOCUMENTS

| | | |
|---|---|---|
| 4,276,211 A | 6/1981 | Singer et al. |
| 4,552,885 A | 11/1985 | Gabriele et al. |
| 4,696,822 A | 9/1987 | Matsumura et al. |
| 5,354,742 A | 10/1994 | Deming et al. |
| 5,938,825 A | 8/1999 | Gaglani et al. |
| 5,939,203 A | 8/1999 | Kappock et al. |
| 6,059,991 A | 5/2000 | Gaglani et al. |
| 6,140,370 A | 10/2000 | Gaglani et al. |
| 6,156,803 A | 12/2000 | Curry et al. |
| 6,353,021 B1 | 3/2002 | Gaglani et al. |
| 6,506,794 B1 | 1/2003 | Sianawati et al. |
| 6,596,779 B1 | 7/2003 | Jean-Noel et al. |
| 6,616,740 B2 | 9/2003 | Winkowski et al. |
| 6,723,256 B1 | 4/2004 | Heller |
| 7,019,046 B2 * | 3/2006 | Narayanan et al. ........... 523/122 |
| 2004/0024099 A1 | 2/2004 | Narayanan et al. |
| 2005/0260240 A1 | 11/2005 | Narayanan et al. |

FOREIGN PATENT DOCUMENTS

| | | |
|---|---|---|
| AU | 8430046 | 1/1986 |
| EP | 0890308 | 1/1999 |
| EP | 1403331 | 3/2004 |
| JP | 11-35408 | 5/1989 |
| JP | 8-295606 | 11/1996 |
| JP | 11-079907 | 3/1999 |
| JP | 11-504030 | 4/1999 |
| JP | 11-506464 | 6/1999 |
| JP | 2001-525346 | 12/2001 |
| WO | 96/33611 | 10/1996 |
| WO | 96/39822 | 12/1996 |
| WO | 99/29176 | 6/1999 |
| WO | 00/11257 | 3/2000 |
| WO | 2005/059239 | 6/2005 |
| WO | 2007/035505 | 3/2007 |

OTHER PUBLICATIONS

PCT, International Search Report and Written Opinion, International Application No. PCT/US07/07432 (Aug. 14, 2008).
JP, Notification of Reasons for Refusal, Japanese Application No. 2009-501608 (Jul. 3, 2012).
AU, Examiner's First Report, Australian Application No. 2007230909 (Feb. 24, 2012).

\* cited by examiner

*Primary Examiner* — John Pak
*Assistant Examiner* — Nathan W Schlientz
(74) *Attorney, Agent, or Firm* — Thompson Hine LLP; William J. Davis

(57) ABSTRACT

A stable, aqueous suspension concentrate which includes a solid polymeric dispersant comprising one or more anionic polymeric dispersing agents, optionally a co-dispersant which preferably is a homopolymer and/or a copolymer of a heterocyclic vinyl lactam, preferably in a wt. ratio of 0.1:1 to 1:0.1, a UV-labile, water-insoluble biocide active, and a UV-blocker or UV-absorber to stabilize said active upon storage and/or exposure to sunlight or UV radiation.

9 Claims, No Drawings

STABLE AQUEOUS SUSPENSION CONCENTRATE FOR DELIVERY OF UV-LABILE WATER-INSOLUBLE BIOCIDES

BACKGROUND OF THE INVENTION

1. Field of the Invention

This invention relates to delivery systems for water-insoluble active chemicals, and, more particularly, to a stable aqueous suspension concentrate of a UV-labile, water-insoluble biocide active concentrate to stabilize such actives against the degradation effects of sunlight and UV-radiation.

2. Description of the Prior Art

Numerous delivery systems and formulations have been proposed to provide aqueous dispersions of substantially water-insoluble biocide active chemicals such as iodopropargyl butyl carbamate (IPBC). For example U.S. Pat. No. 6,506,794 describes an aqueous dispersion of halopropargyl compounds and a partially hydrolyzed polyvinyl alcohol. However, such active dispersions are quite susceptible to degradation upon storage and/or exposure to UV-radiation. In particular, the decomposition of IPBC typically results in the formation of a yellow or brown by-product. The compositions thus will be unsuitable for use in certain systems in need of antimicrobial protection particularly white aqueous paints.

Various methods and compositions have been described to stabilize biocidal compositions containing IPBC, for example, using UV absorbers and/or organic epoxides in a liquid vehicle, as shown in U.S. Pat. Nos. 4,276,211; 4,552,885; 5,938,825; 6,059,991 and 6,140,370. U.S. Pat. No. 6,616,740 teaches on the use of various glycol carriers for IPBC stabilization. However, none of these disclosures provide a stable IPBC composition as an aqueous dispersion free from yellowing on exposure to UV-radiation.

U.S. Pat. No. 6,156,803 discloses the use of a partially neutralized alkyl vinyl ether-maleic acid half ester copolymer as a dispersing agent for water-insoluble agriculturally active chemicals. Published U.S. Patent Application US 2004/0024099 A1 describes an aqueous suspension concentrate for water insoluble chemicals comprising a mixture of an anionic polymeric suspension agent and a homo- and/or a co-polymer of a heterocyclic vinyl lactam.

Accordingly, it is an object of this invention to provide a stable, aqueous suspension concentrate of a UV-labile biocide active for delivery of such active in stabilized form into formulations and onto substrates.

A particular object herein is to provide such stable concentrates which experience substantially no degradation or coloration upon storage and/or exposure to sunlight or UV-radiation while retaining its bioactivity.

SUMMARY OF THE INVENTION

What is described herein is a stable, aqueous suspension concentrate which includes a solid polymeric dispersant comprising one or more anionic polymeric dispersing agents, optionally a co-dispersant which preferably is a homopolymer and/or a copolymer of a heterocyclic vinyl lactam, preferably in a wt. ratio of 0.1:1 to 1:0.1, respectively, a UV-labile, water-insoluble biocide active and a UV-blocker or UV-absorber to stabilize said active upon storage and/or exposure to sunlight or UV-radiation.

Preferably the stable, aqueous suspension concentrate includes a biocide which is a fungicide or preservative.

Most preferably the biocide is a halopropargyl compound, an isothiazolone, a triazole, a phthalimide, benzimidazol carbamate or tetrachloroisophthalonitrile; more particularly, iodopropargyl butyl carbamate (IPBC), benzisothiazolone (BIT), propiconazole, N(trichloromethylthio)pthalimide, methyl benzimidazol-2-yl carbamate or tetrachloroisophthalonitrile.

The UV-blocker or absorber suitably is titanium dioxide, zinc oxide, stilbenes, or UV-blocking minerals and mixtures thereof. The UV-absorbers can be esters of aromatic or aliphatic acids with appropriate substituents, aromatic ketones, triazines, which usually are commercially available.

In one embodiment of the invention, the stable, aqueous suspension concentrate includes a co-dispersant which comprises a homopolymer or copolymer of vinyl pyrrolidone, and an anionic dispersing agent which is an ionic derivative of methyl vinyl ether-maleic acid half-ester.

A feature of the invention is that the suspension concentrate exhibits essentially no degradation on storage at 50° C. for 30 days, and substantially no discoloration or yellowing on exposure to sunlight or UV-radiation.

The invention herein further comprises a composition which includes the stable aqueous suspension concentrate, e.g. a paint composition; or a coating composition, construction material like concrete, bricks, asphalt, shingles, metals and the like; or a personal care composition.

Another feature of the invention is the provision of an article which comprises a substrate coated with the suspension concentrate described alone; e.g. an article wherein said substrate is wood.

DETAILED DESCRIPTION OF THE INVENTION

The primary dispersant in the present solid polymeric dispersant composition of the invention is an anionic polymeric dispersant such as the sodium salt of alkyl vinyl ether/maleic acid half-ester copolymer (Easy-Sperse®) (ISP), a lignosulfonate or metal salt thereof, e.g. POLYFON® or REAX® (Westvaco); a sulfonated naphthalene/formaldehyde condensate, e.g. MORWET® (Witco); UFOXANE® or MARESPERSE® (Lignotech); an alpha-olefin/maleic acid copolymer, a high molecular weight block copolymer with pigment affinic groups, e.g., DISPERBYCK 190 (BYK Chemie) or a polyacrylate, which is capable of dispersing hydrophobic compounds in water, and mixtures thereof. Desirably the monomer of the anionic polymer contains 1-4 anionic sites per mole of repeat units.

The optional co-dispersant in the composition of the invention is a vinyl lactam which is suitably the homopolymer of vinyl pyrrolidone or vinyl caprolactam either optionally substituted on the ring or in the vinyl group with a lower alkyl ($C_1$ to $C_4$ alkyl), or a mixture of these homopolymers. Alternatively, the co-dispersant can be a copolymer of vinyl pyrrolidone and/or vinyl caprolactam, e.g. vinyl pyrrolidone/vinyl caprolactam copolymer, vinyl pyrrolidone/vinyl acetate, vinyl pyrrolidone/acrylic acid, vinyl pyrrolidone/acrylate, vinyl pyrrolidone and butane, or a vinyl pyrrolidone and a $C_{14}$-$C_{24}$ alpha-olefin. The vinyl lactam co-dispersant generally has a weight average molecular weight of between about 5,000 and about 100,000 consistent with a Fikentscher K-value of from about 10 to about 120. The codispersant can be a clay selected from naturally occurring silicates, atta clay, bentonite, diatomaceous earth, and Montmorillonite. In the solid dispersant mixture, the lactam polymer can coil around and coat at least a portion of an active water-insoluble ingredient thus reducing its surface hydrophobicity while retaining the intrinsic hydrophobic character of the insoluble active component. The lactam coating also can associate with anions of the primary dispersant to provide a composition of improved stability and permit high load active compositions for disparate hydrophobic species which are not otherwise suspendable. The use of the co-dispersant lactam polymer in the invention solid mixture permits the use of a lower concentration of the primary anionic polymeric dispersant component which reduces irritant properties and/or foaming. Also the presence of the lactam polymer in the solid mixture allows the use of several otherwise incompatible anionic polymeric dispersants.

The active component of the invention compositions is a particulate, substantially water-insoluble UV-labile biocide compound, or a hydrophobic compound or mixture of such compounds, and is preferably a biocide such as a halopropargyl compound, a isothiazolone, a triazole, a phthalimide, a benzimidazole carbamate, a tetrachloroisophthalonitrile and the like.

Some of these biocide compounds usually exhibit significant degradation upon certain storage conditions and/or exposure to sunlight or UV-radiation accompanied by discoloration when used in such products as in paint, wood or personal care formulations.

By the term "substantially insoluble", it is meant that for all practical purposes, the solubility of the compound in water is insufficient to make the compound practicably usable in a spray-on or dip end use without some modification either to increase its solubility or dispersability in water, so as to increase the compound's bioavailability or avoid the use of excessively large volumes of solvent. Compounds having low water solubility usually include those having a solubility of less than 1 gram per 100 grams of water at room temperature conditions.

Typical "substantially insoluble" biocides include: Iodopropargyl butyl carbamate (IPBC), Benzisothiazolone (BIT), Propiconazole, N(trichloromethylthio)pthalimide, methyl benzimidazol-2-yl carbamate, tetrachloroisophthalonitrile, 2-n-octyl-3-isothiazolone, Dibromonitrilopropri-anamide (DBNPA), 2-(thiocyanomethylthio)benzothiazole (TCMTB), Tebuconazole, Tributyl tin benzoate, Parabens, 2,5-dimethyl-N-cyclohexyl-N-methoxy-3-furan carboxamide, 5-Ethoxy-3-trichloromethyl-1,2,4 thiadiazole, 3-(2-methyl piperidino) propyl 3,4-dichlorobenzoate, N,N'-(1,4-piperazinediyl bis (2,2,2-trichloro)ethylidene) bis formamide, Tetramethyl thiuram disulfide, 0-Ethyl-S,S,diphenyl-dithiophosphate, 5,10-dihydro-5,10-dioxo naphtho (2,3,9)-p-dithiin-2,3-dicarbonitrile, α-2-[(4-chlorophenyl)ethyl]-α-(1, 1-dimethyl ethyl)-1H-1,2,4-triazole-1-ethanol 3-(3,4-dichlorophenyl)1,1 dimethylurea, N-tridecyl-2,6-dimethylmorpholine and 4-N-dodecyl-2,6-dimethylmorpholine.

By the term "UV labile" is meant for all practical purposes, the active ingredient is susceptible to absorption of any part of natural sunlight or exposed artificial light. Generally, any active ingredient containing unsaturated moieties, especially with conjugation, and aromatic or heterocyclic components, will be subject to absorption of such radiation, which eventually can cause a color change degradation or loss of activity.

In this invention, the term UV-blocker and/or UV-absorber includes those compounds which will cause a considerable shift of an appropriate active portion of the radiation spectral component.

The instant invention provides a suspension concentrate which is environmentally friendly, and free of organic solvents and conventional emulsifiers. The aqueous suspension concentrate herein can be formulated with multiple active ingredients to enhance its spectrum of activity. The concentrate is easily dilutable with water. A high salt content in the ground water from the field will not affect its stability on dilution. The suspension concentrate can be made easily by standard methods, as described below:

The commercial product Easy-Sperse® (International Specialty Products Inc.) suitably is employed as the anionic polymeric dispersant in the solid composition of the invention. Easy-Sperse® is the partially neutralized (NaOH) aqueous solution of methyl vinyl ether/maleic acid half-ester (ethyl/butyl) copolymer having a solids content of about 25% and a viscosity of about 6,000 cps.

The optional co-dispersant in the composition suitably is an aqueous solution of polyvinyl pyrrolidone (20-40% solids). A solution/slurry of both the primary and co-dispersant is provided in a weight ratio of these ingredients of 0.1:1 to 1:0.1, respectively, preferably 1:0.5 to 1:5, and, most preferably, 1:1 to 1:4. The solution/slurry may be diluted with water, if necessary, to produce a viscosity particularly suitable for spray drying, e.g. 3,000 to 6,000 cps. Then the solution/slurry is spray dried suitably at an inlet temperature of about 300-480° F. and an outlet temperature of about 150-270° F. The product of the spray drying process is a solid polymeric dispersant concentrate suitable for delivery of UV-labile, water-insoluble biocide actives. If, however, both the primary and co-dispersants are commercially available as solids, then only simple granulation of the ingredients is required to obtain the desired solid concentrate.

The active material then can be added in a suitable amount and processed, if desired, for water-sensitive actives, under anhydrous conditions, and made into solid delivery systems such as wettable powders, water dispersible granules and tablets. If desired, the solid form can be used in an aqueous medium with water of dilution, in an aqueous or suspension formulation. The formulation also can be coated onto hydrophobic surfaces, or printed onto sheets.

The products of the invention are advantageous from a commercial standpoint for the following reasons. In particular the suspension concentrate exhibits essentially no degradation on storage at 50° C. for 30 days, and substantially no discoloration or yellowing on exposure to sunlight or UV-radiation.

The solid composition of the invention also may be efficiently prepared by simply homogenizing and wet-milling the components or by extrusion. The composition may be diluted with a desired amount of water by mixing in a high speed mixer for a period of from about 30 minutes to 1 hour.

The composition of the present invention can incorporate up to 90% of an active material in its mixture while retaining its stability for at least 1 year or more. On dilution the active component can have a concentration of 10 ppm to 50% in the diluted mixture while retaining suspension stability for 4 hours or more. The combination of the anionic dispersant with the lactam polymer has a synergistic suspension effect in that the dispersing ability of the sum of either component alone is markedly exceeded.

Having generally described the invention, reference is had to the following examples which illustrate preferred embodiments and comparisons of the present concentrate or formulation with those of the prior art.

Example 1

Preparation of Solid Polymeric Dispersant Concentrate of Invention 72 g of an Easy-Sperse® solution (24.8% solids) was mixed with 176 g of PVP K-30 (30.5% solids), then homogenized at room temperature for 1 hour and concentrated in a hood overnight at room temperature followed by drying in a vacuum oven (<10 mm Hg) at 80° C. for 2 hours. The resulting solid product had a Tg of 159° C. and <1% bound water and a wt. ratio of Easy-Sperse® to PVP of 1:3.

Example 2

Preparation of Solid Polymeric Dispersant Concentrate by Spray Drying

240 Kg of Easy-Sperse® solution (26% solids) and 720 Kg of PVP K-30 (36.6% solids) were mixed and heated to 120° F. and then diluted with 600 lbs of water. The resulting solution was fed into a commercial spray dryer with an inlet temperature of 410° F. and an outlet temperature of 265° F. A solid was obtained in the form of a powder which passed through a 20 mesh screen. 700 lbs of dry material was obtained with 7% total (bound) water. The wt. ratio of Easy-Sperse® to PVP was 1:4.

Example 3

Examples 1 and 2 were repeated at a wt. ratio of 1:1. Similar results were obtained.

Example 4

Examples 1 and 2 were repeated at a wt. ratio of 1:2. Similar results were obtained.

Example 5

Example 1 was repeated with solid Morwet® D-425 in place of a solution of Easy-Sperse®, and a solution of PVP to produce a 1:1 wt. ratio solid.

Example 6

Example 5 was repeated at a wt. ratio of 1:3 with similar results.

Example 7

Example 5 was repeated with solid Reax® 100M in place of Morwet® D-425 with similar results.

Example 8

Example 6 was repeated with solid Reax® 100M in place of Morwet® D-425 with similar results.

Example 9

Mixture of Solid Dispersant and Biocide Active 700 g of commercial IPBC active was mixed with 80 g of the polymeric dispersant of Example 2 and 220 g of commercially available titanium dioxide in a V-blender. This solid premix was used to formulate wettable powders, suspension concentrates, water-dispersible granules and tablets of the active.

Example 10

700 g commercial BIT active was mixed with 80 g of the polymeric dispersant of Example 2 and 220 g of commercially available titanium dioxide in a V-blender. This solid premix was used to formulate wettable powders, suspension concentrates, water-dispersible granules and tablets of the active.

Example 11

300 g of commercial IPBC was mixed with 70 g of the polymeric dispersant/binder composition of Example 6 and 100 g of commercially available titanium dioxide in a V-blender. This charge was used to produce extruded granules and tablets.

Example 12

100 g of the charge from Example 11 was made into a paste by kneading with water (10-20 g) and was extruded in a laboratory table top extruder at maximum speed. The extrudate was dried in an oven at 70 C for a period of 8 hours. The extrudate was dispersible in water at a use level concentration of IPBC of from 0.1% to 2.0%.

Example 13

50 g of the extrudate of Example 12 was mixed with 1.5 g of cross-linked polyvinyl pyrrolidone (Polyclar® ATF) and several tablets were made by compressing the powder in a laboratory tablet press at a pressure of 2.5 tons. Each tablet weighed about 3 g, containing approximately 1.86 g IPBC. Aqueous suspensions were made by dispersing each tablet in 186 g water by mild agitation for about 10 minutes, to produce a 1% IPBC suspension.

Example 14

The following briefly describes the procedure used to prepare suspension concentrates of biocides shown in the following Examples 15A to 15D.

Compositions of biocide suspension concentrates in suitable and preferred ranges by weight thus-prepared include: Active ingredient: 5-50%; preferred range 10-40%; polymeric dispersant; 0.2-8%, preferred: 1-5%; UV-blocker: 0.2-20%, preferred: 2-10%; thickener: 0.05-0.4%; preferred: 0.1-0.3%; wetting agent: 0-1.0%, preferred: 0-0.5%; defoamer: 0.05-0.4%, preferred: 0.1-0.3%; preservative: 0-0.5% preferred 0-0.2%; and water to 100%.

General Procedure:

In a vessel with Cowles mixer added about 80% of water required, followed by wetting agent, dispersant, UV-blocker, and active ingredient. Mixed at 500 rpm for 30 minutes. Defoamer and thickener were added to the above mixture and remaining water, and mixed at 2000 rpm for an additional 30 minutes. The charge was pumped into a basket mill and milled to the selected particle size, usually about 10 microns average particle size (a Hegman rating between 6 and 7).

Thickeners used are usually commercially available water soluble polymers that impart high viscosity when added at very low concentrations, such as natural gums, carbohydrates like Kelzan®, synthetic polymers like Carbopol® (polyacrylates). The wetting agents are used to reduce friction during high speed grinding, usually low foaming organic liquids with a low dynamic surface tension, e.g. Surfynol® series or N-octyl pyrrolidone. Preservatives used are commercially available registered organic compounds capable of controlling biological growth in aqueous medium during a reasonable storage period of about 1-5 years, e.g. Nuosept® series, Kathon®, Proxel® and the like.

Example 15 A

1 Kg of an aqueous suspension concentrate was prepared using about 200 g of commercially available IPBC, by the general procedure described in Example 14. 220 g IPBC was mixed with 25 g Easy-Sperse® P 20 polymeric dispersant and 600 g deionized water. The charge was loaded in a blender at low speed followed by high speed blending for a period of 30 minutes. During the blending process, 1.0 g Surfynol® 104 E was added along with 1.0 g Sag 30. The charge was processed as in Example 14. The suspension concentrate was then mixed with 122 g of 1% Kelzan® stock solution prepared separately, followed by addition of the remaining quantity of water (53 g) to make up a 22% IPBC concentrate.

Example 15 B

Example 15 A was repeated except that 50 g zinc oxide was included in the initial solid mix with water and 3 g of make-up water was used at the end instead of 53 g water.

Example 15 C

Example 15 B was repeated except that titanium dioxide was used in the place of zinc oxide.

Example 15 D

Example 15 C was repeated using 400 g IPBC instead of 200 g and 40 g Easy-Sperse® P 20 instead of 25 g and initial water was 400 g instead of 600 g, and make-up water was 23 g.

Example 15 E

Example 15 C was repeated except that Disperbyck 190 was used in place of Easy-Sperse.

The suspension concentrates described in Example 15 A, 15 B, and 15 C were evaluated for yellowing on exposure to UV-light. The results are shown in Example 16. Examples 15 C and 15 E were evaluated for accelerated storage stability. These results are shown in Example 17. Example 15 D was evaluated as an additive in paint. These results are shown in Example 18.

Example 16

TABLE 1

| Yellowing upon UV-light Exposure | |
|---|---|
| Formulation | Degree of Yellowing |
| Formulation 15 A | +++ |
| Formulation 15 B | + |
| Formulation 15 C | − |

"+" = yellowing;
"−" = non-yellowing

Example 17

Stability of IPBC in Aqueous Suspension Concentrate

The IPBC dispersion described in Example 15 C and 15 E was heat aged for 30 days at 50° C. The resultant IPBC levels were determined by Reversed-Phase HPLC. The levels of IPBC detected in Sample 15 C was 21.54±0.06 which is the same level as the sample analyzed at time zero, immediately after preparation of the suspension concentrate. Levels of IPBC detected in Sample 15 E were 20.34±0.2% which is the same level as the sample analyzed at time zero.

Example 18

The efficacy of the 40% IPBC suspension concentrate in Example 15 D, was compared to that of a commercial IPBC formulation comparable in strength following ASTM D5590 entitled "Determining the Resistance of Paint Films and Related Coatings to Fungal Defacement by Accelerated Four Week Agar Plate". The results are shown in Table 2. Growth ratings were taken every 7 days, on a scale of "0" to "10", where "0" corresponds to the complete absence of fungal growth and "10" corresponds to the complete coverage by fungus. The Mixed Inoculum contained the fungi *Aspergillus niger* and *Penicillium funiculosum*.

TABLE 2

| Efficacy of IBPC Aqueous Suspension Concentrate | | | | | | | | | |
|---|---|---|---|---|---|---|---|---|---|
| | | Mixed Inoculum | | | | | | | |
| | % by | Leached | | | | Unleached | | | |
| Paint | Wt. | 1 | 2 | 3 | 4 | 1 | 2 | 3 | 4 |
| White Exterior | | | | | | | | | |
| Susp. Conc. | 0.6 | 0 | 0 | 0 | 1 | 0 | 0 | 0 | 0 |
| Commercial | 0.6 | 0 | 0 | 0 | 0 | 0 | 0 | 0 | 0 |
| Control | — | 5 | 9 | 10 | 10 | 3 | 3 | 3 | 5 |
| Deep Tint | | | | | | | | | |
| Susp. Conc. | 0.5 | 0 | 0 | 0 | 1 | 0 | 0 | 0 | 0 |
| Commercial | 0.5 | 0 | 0 | 0 | 1 | 0 | 0 | 0 | 0 |
| Control | — | 7 | 7 | 8 | 10 | 4 | 4 | 8 | 10 |

Example 19

1 Kg of an aqueous suspension concentrate was prepared with BIT following the procedure of Example 15 C.

Example 20

The efficacy of the BIT dispersion described in Example 19 was compared to that of a commercial BIT formulation of similar strength following ASTM D2574 entitled "Resistance of Emulsion Paints in the Container to Attack by Microorganisms". Results are shown in Table 3. Growth ratings were taken at day 1, 2, 3 and 6 after each bacterial challenge on a scale of "0" to "4"; where "0" corresponds to no growth, "1" is less than 10 cfu/ml, "2" is 11-100 cfu/ml; "3" is 101-1,000 cfu/ml and "4" is higher than 1,000 cfu/ml. The mixed bacterial inoculum consisted of *Pseudomonas aeruginosa, Enterobacter cloacae, Bacillus subtilis, Bacillus megaterium* and *Bacillus licheniformis*. Final concentration for Challenge I was $1.52 \times 10^6$ cfu/ml and for Challenge II, $1.56 \times 10^7$ cfu/ml.

TABLE 3

Efficacy of BIT Aqueous Suspension Concentrate

| Paint | % by Wt. | Challenge I | | | | Challenge II | | | |
|---|---|---|---|---|---|---|---|---|---|
| | | 1 | 2 | 3 | 6 | 1 | 2 | 3 | 6 |
| Paint A | | | | | | | | | |
| Susp. Conc. | 0.05 | 0 | 0 | 0 | 0 | 0 | 0 | 0 | 0 |
| Commercial | 0.05 | 0 | 0 | 0 | 0 | 0 | 0 | 0 | 0 |
| Control | — | 4 | 4 | 4 | 4 | 4 | 4 | 4 | 4 |
| Paint B | | | | | | | | | |
| Susp. Conc. | 0.1 | 0 | 0 | 0 | 0 | 1 | 0 | 0 | 0 |
| Commercial | 0.1 | 0 | 1 | 0 | 0 | 0 | 0 | 0 | 0 |
| Control | — | 4 | 4 | 4 | 4 | 4 | 4 | 4 | 4 |

Example 21

Example 15 was repeated using propiconazole instead of IPBC. Similar results were obtained.

Example 22

Example 19 was repeated using a combination of IPBC and propiconazole in the weight ratio of 1:2. Similar results were obtained.

Example 23

Example 15 was repeated using Folpet instead of IPBC. Similar results were obtained.

Example 24

Example 15 was repeated using chlorothalonil. Similar results were obtained.

While the invention has been described with particular reference to certain embodiments thereof, it will be understood that changes and modifications may be made which are within the skill of the art.

What is claimed is:

1. A stable, aqueous suspension concentrate which includes a solid polymeric dispersant comprising one or more anionic polymeric dispersing agents and a polyvinyl pyrrolidone co-dispersant, wherein said anionic polymeric dispersing agent and said co-dispersant are present in a wt. ratio of 0.1:1 to 1:0.1, and further comprising iodopropargyl butyl carbamate (IPBC) and titanium dioxide wherein said IPBC is stable upon storage and/or exposure to sunlight or UV radiation and wherein the IPBC does not degrade upon storage for 30 days at 50° C.

2. A stable, aqueous suspension concentrate according to claim 1 wherein said anionic polymeric dispersing agent is selected from the group consisting of a sodium salt of alkyl vinyl ether/maleic acid half ester copolymer, a lignosulfonate or metal salt thereof, a sulfonated naphthalene/formaldehyde condensate, an alpha-olefin/maleic acid copolymer, a polyacrylate and mixtures thereof.

3. A stable, aqueous suspension concentrate according to claim 1 wherein said anionic polymeric dispersing agent is an ionic derivative of methyl vinyl ether-maleic acid half-ester.

4. A stable, aqueous suspension concentrate according to claim 1 wherein said concentrate is free of organic solvents.

5. A composition including the concentrate of claim 1.

6. A paint composition including the concentrate of claim 1.

7. A personal care composition including the concentrate of claim 1.

8. An article comprising a substrate coated with the suspension concentrate of claim 1.

9. An article according to claim 8 wherein said substrate is wood.

* * * * *